(12) United States Patent
Brannan

(10) Patent No.: US 10,792,100 B2
(45) Date of Patent: Oct. 6, 2020

(54) SYSTEMS AND METHODS FOR SPHERICAL ABLATIONS

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 1053 days.

(21) Appl. No.: 14/831,467

(22) Filed: Aug. 20, 2015

(65) Prior Publication Data

US 2016/0051327 A1    Feb. 25, 2016

Related U.S. Application Data

(63) Continuation of application No. 62/039,793, filed on Aug. 20, 2014.

(51) Int. Cl.
*A61B 18/18* (2006.01)
*A61B 34/20* (2016.01)
*A61B 18/00* (2006.01)

(52) U.S. Cl.
CPC .......... *A61B 18/1815* (2013.01); *A61B 34/20* (2016.02); *A61B 2018/00023* (2013.01);
(Continued)

(58) Field of Classification Search
CPC ................ A61B 18/18; A61B 18/1815; A61B 2018/1815; A61B 2018/1861; A61B 2018/00744

See application file for complete search history.

(56) References Cited

U.S. PATENT DOCUMENTS

| 6,188,355 B1 | 2/2001 | Gilboa |
| 6,379,349 B1 | 4/2002 | Muller et al. |

(Continued)

FOREIGN PATENT DOCUMENTS

| CN | 101511295 A | 8/2009 |
| CN | 203483507 U | 3/2014 |

(Continued)

OTHER PUBLICATIONS

International Search Report dated Nov. 24, 2015 in corresponding International Application No. PCT/US2015/046122, 3 pages.

(Continued)

*Primary Examiner* — Ronald Hupczey, Jr.

(57) ABSTRACT

A system including a catheter navigable to a location within a patient, a lumen extending through the catheter and ending at the distal end in an orifice, a fluid controller in fluid communication with the lumen of the catheter and capable of supplying a fluid to or removing a fluid from an area proximate the desired location. The control of the fluid in the area proximate the desired location affecting a dielectric constant of the area proximate the desired location. The system includes a microwave energy source, and a microwave ablation probe connected to the microwave energy source, the microwave ablation probe being navigable to a desired location within the patient. Application of energy from the microwave energy source to the microwave ablation probe in an area proximate the desired location having the affected dielectric constant results in a substantially spherical tissue effect in the area proximate the desired location.

20 Claims, 9 Drawing Sheets

(52) U.S. Cl.
CPC ............... *A61B 2018/00541* (2013.01); *A61B 2018/00577* (2013.01); *A61B 2018/00666* (2013.01); *A61B 2018/00744* (2013.01); *A61B 2018/00785* (2013.01); *A61B 2018/00797* (2013.01); *A61B 2018/00821* (2013.01); *A61B 2018/00904* (2013.01); *A61B 2018/00982* (2013.01); *A61B 2018/1838* (2013.01); *A61B 2018/1846* (2013.01); *A61B 2018/1853* (2013.01); *A61B 2018/1861* (2013.01); *A61B 2018/1892* (2013.01); *A61B 2034/2051* (2016.02); *A61B 2218/002* (2013.01); *A61B 2218/007* (2013.01)

(56) References Cited

U.S. PATENT DOCUMENTS

| | | | |
|---|---|---|---|
| 6,673,070 B2 * | 1/2004 | Edwards | A61B 18/1206 606/101 |
| 8,568,401 B2 | 10/2013 | Brannan | |
| 9,044,254 B2 | 6/2015 | Ladtkow et al. | |
| 2005/0245920 A1 * | 11/2005 | Vitullo | A61B 18/18 606/33 |
| 2009/0129646 A1 * | 5/2009 | Zwirn | A61B 5/0046 382/128 |
| 2009/0187180 A1 | 7/2009 | Brannan | |
| 2010/0146673 A1 | 6/2010 | Riemenschneider et al. | |
| 2011/0054458 A1 * | 3/2011 | Behnke | A61B 18/18 606/33 |
| 2011/0077635 A1 | 3/2011 | Bonn | |
| 2011/0118724 A1 | 5/2011 | Turner et al. | |
| 2012/0053513 A1 | 3/2012 | Tada et al. | |
| 2013/0034569 A1 | 2/2013 | Smith et al. | |
| 2013/0131496 A1 * | 5/2013 | Jenkins | A61B 5/055 600/411 |
| 2014/0046174 A1 * | 2/2014 | Ladtkow | A61B 1/018 600/424 |
| 2014/0046176 A1 | 2/2014 | Ladtkow et al. | |
| 2014/0270441 A1 | 9/2014 | Baker | |
| 2014/0276033 A1 | 9/2014 | Brannan et al. | |
| 2014/0276739 A1 | 9/2014 | Brannan et al. | |
| 2014/0281961 A1 | 9/2014 | Baker | |
| 2014/0282216 A1 | 9/2014 | Baker | |
| 2015/0141809 A1 | 5/2015 | Costello et al. | |
| 2015/0141869 A1 | 5/2015 | Costello et al. | |
| 2015/0265257 A1 | 9/2015 | Costello et al. | |

FOREIGN PATENT DOCUMENTS

| | | | |
|---|---|---|---|
| WO | 00/10456 A1 | 3/2000 | |
| WO | 01/67035 A1 | 9/2001 | |
| WO | 02/38038 A2 | 5/2002 | |
| WO | 2007/024878 A1 | 3/2007 | |
| WO | 2013/106054 A2 | 7/2013 | |
| WO | WO-2013106054 A2 * | 7/2013 | ......... A61B 18/1815 |
| WO | 2014/025549 A1 | 2/2014 | |

OTHER PUBLICATIONS

Extended European Search Report for application No. 15834303.8 dated Feb. 5, 2018 (8 pages).
Australian Examination Report issued in corresponding Appl. No. 2015305374 dated Apr. 26, 2019 (3 pages).
Office Action issued in corresponding Japanese Appl. No. 2017-508995, dated Jul. 17, 2019, toegether with English language translation (10 pages).
Chinese office action issued in CN Application No. 201580044493.1, dated Jul. 26, 2018.
Chinese Office Action issued in corresponding Appl. No. CN 201580044493.1 dated May 21, 2019, together with English language translation (14 pages).
Japanese Notice of Allowance issued in corresponding Appl. No. JP 2017-508995 dated Jan. 15, 2020, together with English language translation (5 pages).

* cited by examiner

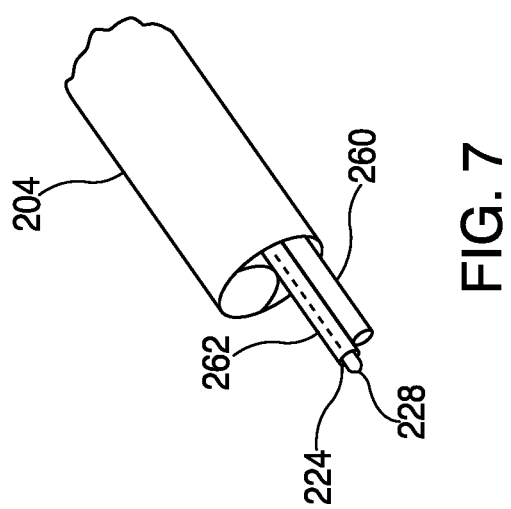
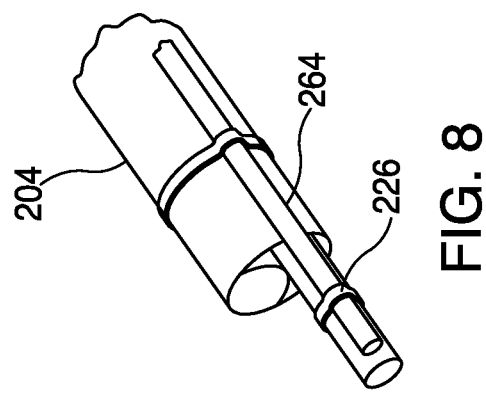
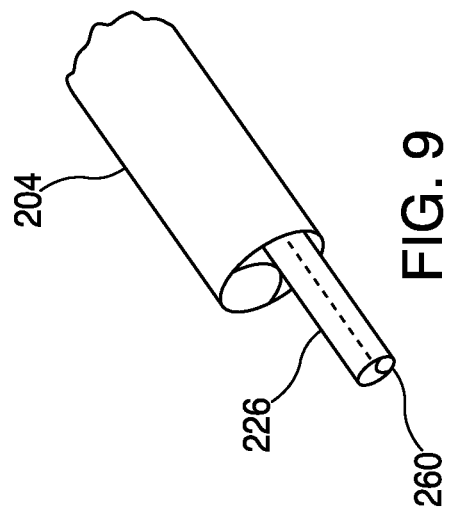

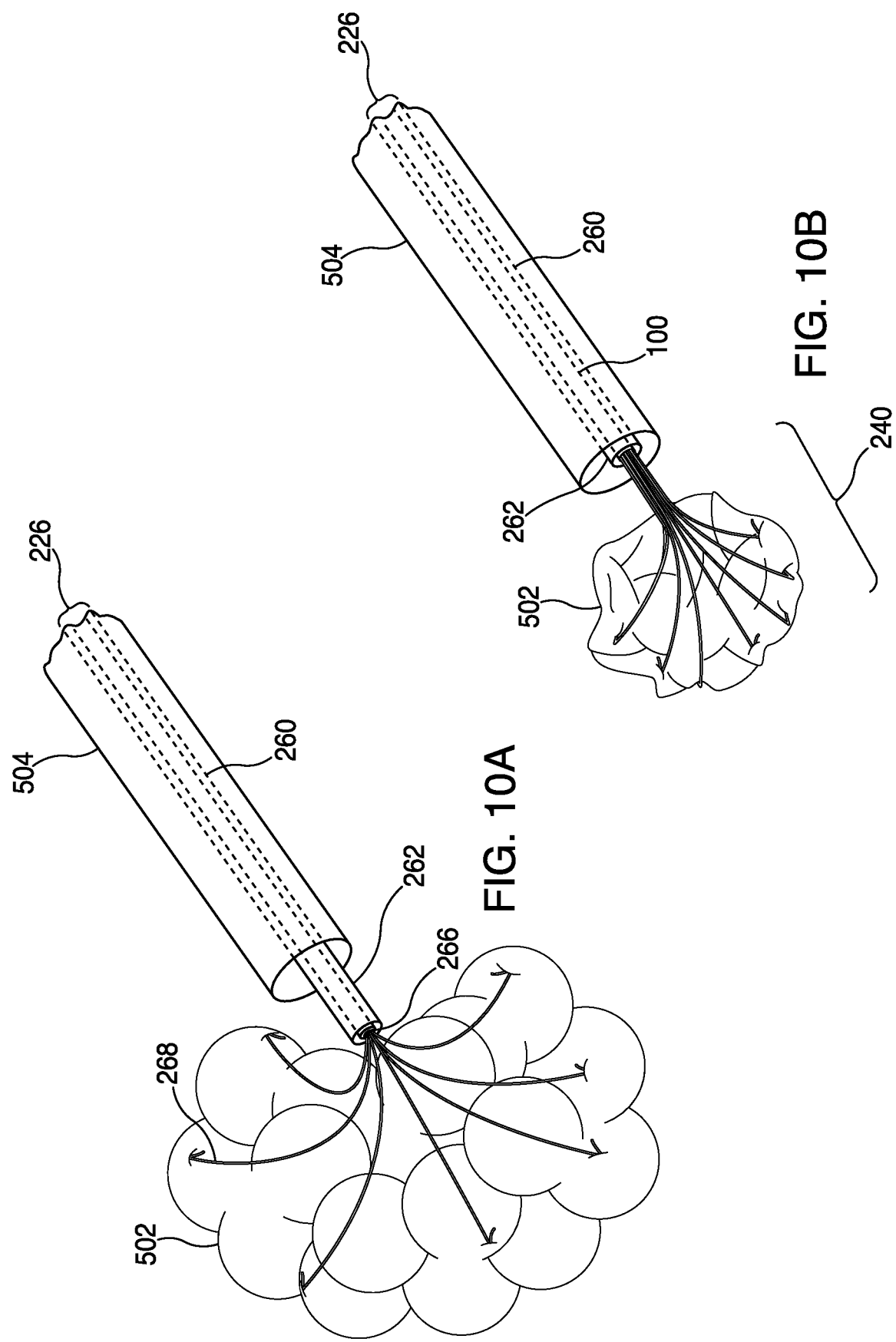

SYSTEMS AND METHODS FOR SPHERICAL ABLATIONS

CROSS-REFERENCE TO RELATED APPLICATIONS

This application claims the benefit of and priority to U.S. Provisional Patent Application No. 62/039,793, filed on Aug. 20, 2014, the entire contents of which are incorporated by reference herein for all purposes.

BACKGROUND

1. Technical Field

The present disclosure relates generally to microwave ablation and, more particularly, to systems and methods of utilizing microwave ablation applicators and peripheral components to generate spherical ablations.

2. Discussion of Related Art

Electromagnetic fields can be used to heat, modify, and destroy tumors. For example, treatment for cancerous cells may involve inserting ablation probes into tissues where cancerous tumors have been identified, and once the ablation probes are properly positioned, the ablation probes induce electromagnetic fields within the tissue surrounding the ablation probes to kill the tumorous cells.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source, and a surgical instrument, e.g., a microwave ablation probe having an antenna assembly, for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed there between. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The heating of tissue for thermal ablation is accomplished through a variety of approaches, including conduction of heat from an applied surface or element, ionic agitation by electrical current flowing from an electrode to a ground pad, optical wavelength absorption, or, in the case of microwave ablation, by dielectric relaxation of water molecules within an antenna electromagnetic field. The ablation zone can be broken down into two components: an active ablation zone and a passive ablation zone.

The active ablation zone is closest to the ablation device and encompasses the volume of tissue which is subjected to energy absorption high enough to assure thermal tissue destruction at a given application time in all but areas of very rapidly flowing fluids, such as around and within large blood vessels or airways. The active ablation zone size and shape is determined by ablation device design. The active ablation zone can therefore be used to produce predictable ablative effects over a given shape and volume of tissue. Ablation within the active ablation zone occurs quickly, typically within 5 minutes.

The passive ablation zone surrounds the active zone and encompasses the volume of tissue which experiences a lower intensity of energy absorption. The tissue within the passive ablation zone may or may not experience tissue destruction at a given application time. Physiological cooling may counter heating from the lower level energy absorption and therefore not allow for sufficient heating to occur within the passive zone to kill tissue. Diseased or poorly perfused tissue within the passive zone may be more prone to heating than other tissues and may also be more susceptible to heat conduction from hotter areas within the ablation zone. The passive zone in these cases can result in unexpectedly large ablation zones. Due to these varying scenarios across space within a targeted physiology, relying on the passive zone to perform thermal ablation is challenging with unpredictable outcomes.

As electromagnetic fields can be induced at a distance by microwave probes, microwave ablation has the potential to create large active zones whose shapes can be determined and held constant by design. Furthermore, the shape and size can be determined through design to fit a specific medical application. By utilizing a predetermined active zone to create a predictable ablation zone, and not relying upon the indeterminate passive ablation zone, microwave ablation can provide a level of predictability and procedural relevance not possible with other ablative techniques.

The shape of the active zone about an antenna is determined by the frequency of operation, the geometry of the antenna, the materials of the antenna, and the medium surrounding the antenna. Operating an antenna in a medium of dynamically changing electrical properties, such as heating tissue, results in a changing shape of the electromagnetic field, and therefore a changing shape of the active zone. To maintain the shape of the active zone about a microwave antenna, the degree of influence on the electromagnetic field of the surrounding medium's electrical properties is reduced.

The size of the active zone about an antenna is determined by the amount of energy which can be delivered from the microwave generator to the antenna. With more energy delivered to the antenna, larger active zones can be generated. To maximize energy transfer from a microwave generator through waveguides and to a microwave antenna requires each system component to have the same impedance, or to be impedance matched. Whereas the impedance of the generator and waveguides are typically fixed, the impedance of a microwave antenna is determined by the frequency of operation, the geometry of the antenna, the materials of the antenna, and the medium surrounding the antenna. Operating an antenna in a medium of dynamically changing electrical properties, such as within heating tissue, results in a changing antenna impedance and varied energy delivery to the antenna, and, as a result, a changing size of the active zone. To maintain the size of the active zone about a microwave antenna, the degree of influence on the antenna impedance of the surrounding medium's electrical properties must be reduced.

In thermal ablation, the primary cause of active zone size and shape change is an elongation of the electromagnetic wave. Wavelength elongation occurs in heating tissue due to tissue dehydration. Dehydration reduces the dielectric constant, elongating the wavelength of microwave fields. Wavelength elongation is also encountered when a microwave device is used across various tissue types due to the varying dielectric constant between tissue types. For example, an electromagnetic wave is significantly longer in lung tissue than in liver tissue.

Wavelength elongation compromises the focus of microwave energy on the targeted tissue. With large volume ablation, a generally spherical active zone is preferable to focus the energy on generally spherical tissue targets. Wavelength elongation causes the electromagnetic field to stretch down along the length of the device toward the generator, resulting in a generally comet- or "hot-dog"-shaped active zone.

Wavelength elongation can be significantly reduced in medical microwave antennas by dielectrically buffering the antenna geometry with a material having an unchanging dielectric constant, as described in U.S. Application Pub. Nos. 2014/0276033 and 2014/0046174, the disclosures of which are incorporated by reference herein. The material of unchanging dielectric constant surrounds the antenna, reducing the influence of the tissue electrical properties on antenna wavelength. By controlling wavelength elongation through dielectric buffering, the antenna impedance match and field shape can be maintained, enabling a large active ablation zone with a predetermined and robust shape.

By providing dielectric buffering with a circulated fluid, such as with saline or water, the high dielectric constants of these materials can be leveraged in the antenna geometry design, and furthermore the circulated fluid can be used to simultaneously cool the microwave components, including the coaxial feed line and antenna. Cooling of the microwave components also enables higher power handling of the components which can be used to deliver more energy to the antenna to create larger active zones.

As described above, the shape of the active zone about an antenna is determined, in part, by the geometry of the antenna. Ordinary ablation antennas do not utilize antenna geometry in combination with wavelength buffering to effectively control microwave field shape. These antennas do not create spherical active zone shapes nor are the active zones robust and unchanging across tissue types or during tissue heating. These antennas allow microwave energy to spread along the external conductor of the device from the device tip towards the generator. The spreading of microwave energy along the shaft results in comet or "hot-dog" shaped active zones.

Microwave antennas can be equipped with a balun or choke, a component of the antenna geometry that improves impedance matching and also can aid in focusing microwave energy into a predetermined shape. When combined with wavelength buffering, a balun or choke can effectively block the backwards propagation of electromagnetic waves along the external conductor toward the generator across various tissue types and during tissue heating, focusing the energy into a robust spherical active zone.

One implementation of a balun includes a balun dielectric that is disposed on the outer conductor of a coaxial cable and an outer balun conductor disposed on the balun dielectric. The balun creates a short section of coaxial waveguide arranged about the inner coaxial cable where the outer conductor of the coaxial cable is the inner conductor of the balun. The balun is disposed about the coaxial cable near the feed of the antenna and in one implementation has a length of $\lambda/4$ where $\lambda$ is the wavelength of the electromagnetic wave within the balun. The balun outer conductor and inner conductor are shorted together at the proximal end to create a $\lambda/4$ short-circuited balun.

One way of describing the function of a $\lambda/4$ short-circuited balun is as follows: an electromagnetic wave propagates proximally along the radiating section of the antenna, enters the balun, reflects off of the short-circuited proximal end of the balun, propagates forward to the distal end of the balun, and exits the balun back onto the antenna radiating section. With this arrangement of balun length, when the electromagnetic wave reaches the distal end of the balun and travels back onto the antenna radiating section, the electromagnetic wave has accumulated a full $\lambda$ of phase change. This is due to the $\lambda/4$ distance traveled forward within the balun, the $\lambda/4$ distance traveled backward within the balun and a $\lambda/2$ phase change which occurs with the reflection off of the short-circuited proximal end of the balun. The result is an electromagnetic wave which, rather than propagating along the external surface of the cable toward the generator, is a wave which is redirected back toward the distal tip of the antenna in coherent phase with the other waves on the antenna radiating section.

The balun, however, substantially increases the diameter of the microwave antenna as well as the needle through which the microwave antenna passes. The size of the needle may limit the uses for the microwave antenna in minimally-invasive procedures, especially when there are repeated treatments.

While the generation of spherical ablations has been demonstrated as feasible in commercial products such as the Emprint™ microwave ablation system, improvements to such systems are always desirable.

SUMMARY

A system including a catheter navigable to a desired location within a patient, a lumen extending through the catheter and ending at the distal end of the catheter in an orifice, and a fluid controller in fluid communication with the lumen of the catheter and capable of supplying a fluid to or removing a fluid from an area proximate the desired location, wherein control of the fluid in the area proximate the desired location affects a dielectric constant of the area proximate the desired location. The system includes a microwave energy source and a microwave ablation probe connected to the microwave energy source, the microwave ablation probe being navigable to a desired location within the patient, wherein application of energy from the microwave energy source to the microwave ablation probe in an area proximate the desired location having the affected dielectric constant results in a substantially spherical tissue effect in the area proximate the desired location.

According to further aspects the system includes an electromagnetic navigation system to facilitate navigation of the catheter and the microwave ablation probe to the desired location and the catheter or the ablation probe may include an electromagnetic sensor associated with the electromagnetic navigation system to identify its location in an electromagnetic field.

According to a further aspect the fluid controller is a vacuum source and the vacuum source may apply suction via the catheter to the area proximate the desired location to affect the dielectric constant of the area proximate the desired location. The suction may remove one or more of air, blood, or mucus. Further, the suction may collapse the tissue in the area proximate the desired location. Still further, the system may include a one-way valve inserted in the patient proximate the desired location, wherein the one-way valve prevents fluid from flowing into the area proximate the desired location to which suction is applied. Alternatively or additionally the system may include a tamponade inflated proximate the desired location, wherein the tamponade prevents fluid from flowing into the area proximate the desired location to which suction is applied.

According to a further aspect of the disclosure, the fluid controller is a fluid supply. The fluid supply may inject a fluid into the area proximate the desired location to affect the dielectric constant of the area proximate the desired location. The fluid may be saline. Alternatively the fluid may include hydrophilic component to attract bodily fluid to the area proximate the desired location. The hydrophilic component may be a salt. Alternatively, the fluid may include a hydrophobic component to repel bodily fluids away from the area proximate the desired location.

The system may further include a one-way valve inserted in the patient proximate the desired location, wherein the one-way valve prevents fluid from flowing from the area proximate the desired location into which the fluid was supplied. Alternatively or additionally the system may include a tamponade inflated proximate the desired location, wherein the tamponade prevents fluid from flowing out of the area proximate the desired location into which the fluid was supplied.

In accordance with a further aspect of the disclosure, the dielectric constant of the fluid supplied to the area proximate the desired location is substantially the same as that of a cooling fluid circulating through the microwave ablation probe.

According to yet another aspect of the present disclosure, the distal end of the microwave ablation probe is exposed and the cooling fluid for the microwave ablation probe is used as the fluid injected into the area proximate the desired location to affect the dielectric constant of the area proximate the desired location.

In yet a further aspect of the present disclosure, the system includes a balun formed on the microwave ablation probe to control the electromagnetic field emanating from the microwave ablation probe.

BRIEF DESCRIPTION OF THE DRAWINGS

Objects and features of the presently disclosed systems and methods of utilizing microwave ablation applicators and peripheral components to generate spherical ablations will become apparent to those of ordinary skill in the art when descriptions of various embodiments thereof are read with reference to the accompanying drawings, of which:

FIG. 7 depicts a multi-lumen extended working channel extending from a bronchoscope in accordance with at least one aspect of the present disclosure;

FIG. 8 depicts an extended working channel extending from a bronchoscope and a catheter in sidecar arrangement in accordance with at least one aspect of the present disclosure;

FIG. 9 depicts a multi-lumen extended working channel extending from a bronchoscope in accordance with at least one aspect of the present disclosure;

FIG. 10A depicts a tool and method of gathering tissue in a first position in accordance with at least one aspect of the present disclosure;

FIG. 10B depicts the tool and method of gathering tissue of FIG. 10A in a second position in accordance with at least one aspect of the present disclosure.

DETAILED DESCRIPTION

The present disclosure is directed to improved systems and methods that utilize thermal control (e.g., antenna cooling), field control (e.g., use of a balun), and wavelength control (e.g., affecting dielectric constant) to generate spherical ablations, maximize the active ablation zone, and provide for predictable treatment results.

Figure 1:
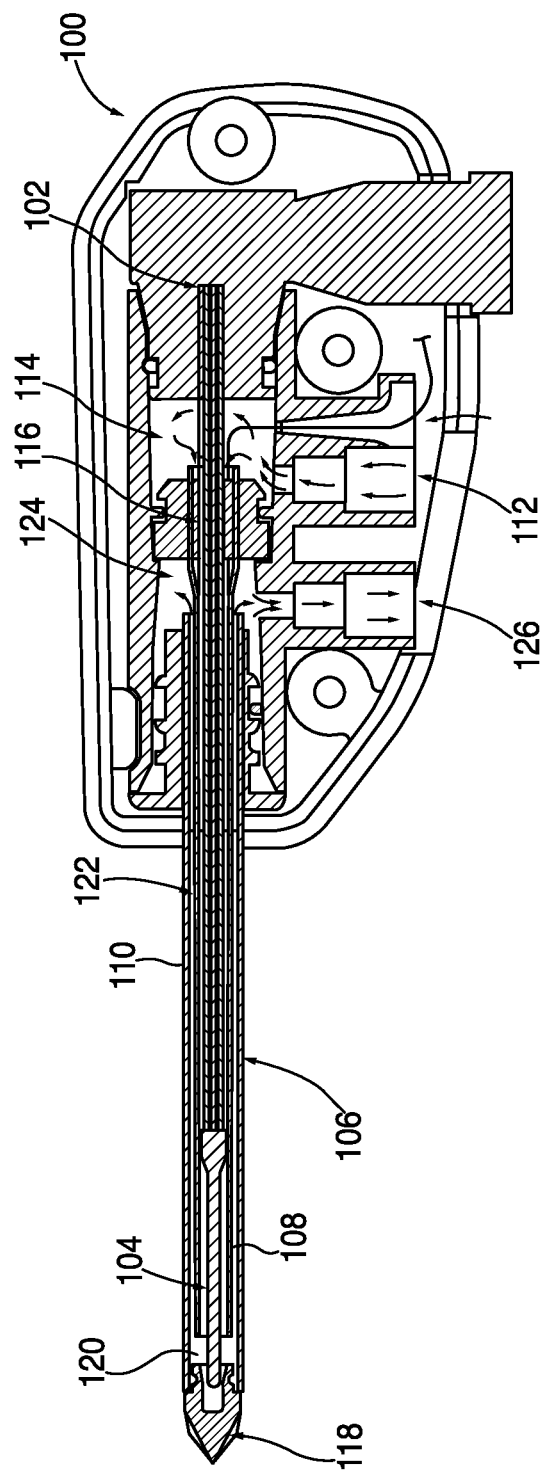
FIG. 1 depicts a cross-sectional view of an ablation probe in accordance with at least one aspect of the present disclosure.

Of the three types of control noted above, two have been previously addressed and the third has been partially addressed by the development of the EMPRINT™ ablation system. As shown in FIG. 1 there is depicted a water jacketed microwave ablation probe 100 including a hub 101 and a feedline 102 having proximal and distal radiating sections 104, 106 formed thereon. Details of the proximal and distal radiating sections 104 and 106 are depicted in more detail in FIG. 2A.

As depicted in FIG. 1, surrounding feedline 102, distal radiating section 104, and proximal radiating section 106 are an inner cooling jacket 108 and an outer cooling jacket 110. Cooling fluid flows through an inflow port 112 and into an inflow chamber 114. The inflow chamber 114 is fluidly connected to the inner cooling jacket 108 and cooling fluid is allowed to flow in the gap 116 between the inner cooling jacket 108 and the feedline 102. Cooling fluid flows along the feedline 102, the proximal radiating section 106 and the distal radiating section 104 and exits the gap 116 proximate the distal tip 118 of the ablation probe 100. Cooling fluid exits the gap 116, circulates around chamber 120 to cool the distal radiating section 104, and then enters a second gap 122 formed between the inner cooling jacket 108 and the outer cooling jacket 110. The outer cooling jacket 110 also forms the shaft of the ablation probe 100 and provides the stiffness and support for insertion of the ablation probe 100 into the patient. Cooling fluid continues to flow proximally through second gap 122 and away from the distal tip 118 until it empties into an outflow chamber 124 and out an outflow port 126. Further construction details of a microwave ablation probe as depicted in FIG. 1 can be found in U.S. Patent Application Pub. No. 2014/0276739, entitled "MICROWAVE ENERGY DELIVERY DEVICE AND SYSTEM," the entire contents of which are incorporated herein by reference.

Figure 2A:
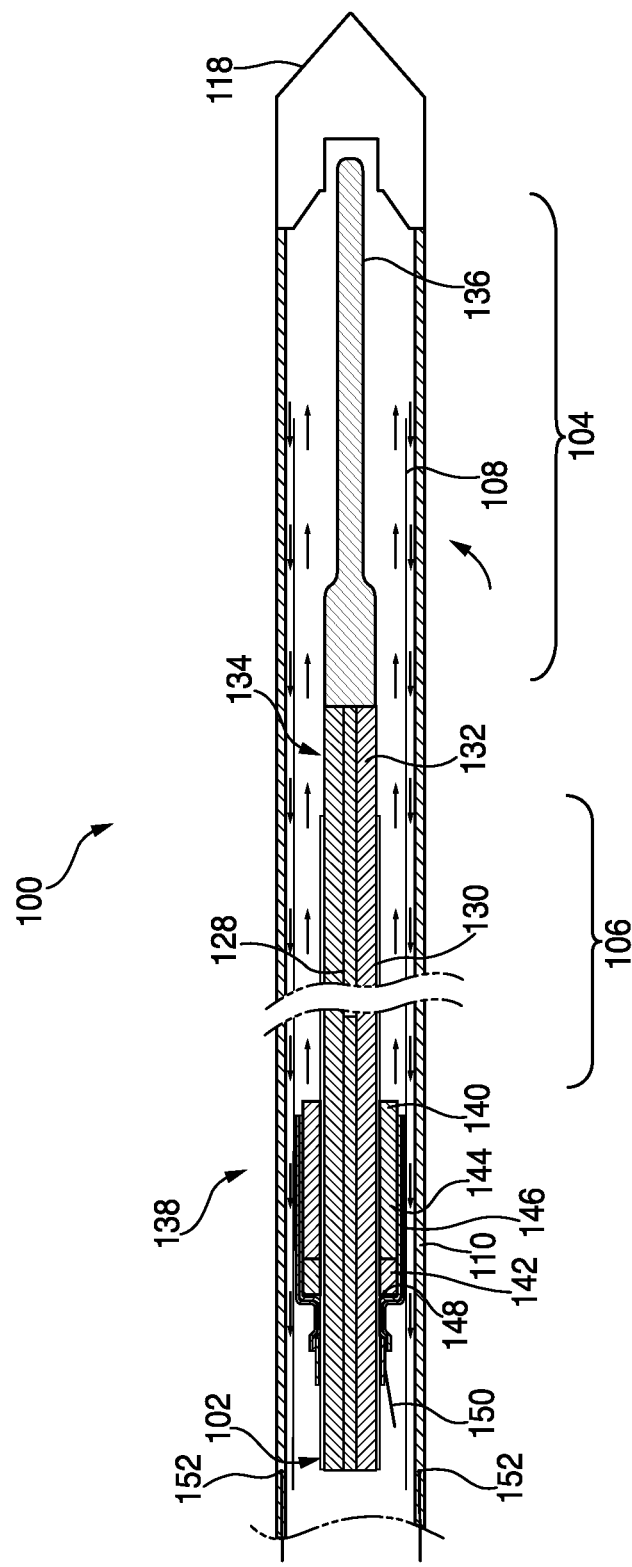
FIG. 2A depicts a detailed cross-sectional view of the distal end of an ablation probe in accordance with at least one aspect of the present disclosure.

FIG. 2A depicts a detailed view of the structure of the microwave ablation probe 100 proximate the distal tip 118. As shown in FIG. 2A, the feedline 102 is comprised of an inner conductor 128, an outer conductor 130 and an insulator 132 formed there between. Between the proximal radiating section 106 and the distal radiating section 104, a portion of the outer conductor 130 of the feedline 102 is removed exposing the insulator 132 and forming a feed gap 134. The inner conductor 128 extends through the insulator 132 of the feed gap 134 and connects to a radiator 136 forming the distal radiating section 104.

A balun or choke 138 is formed proximal the proximal radiating section 106. The balun 138 is formed of an insulator 140 circumscribing the outer conductor 130 and a balun short 142 also circumscribing the outer conductor 130 and formed proximal the insulator 140. Circumscribing the insulator 140 and the balun short 142 is a conductive film 144 and a non-conductive film 146 (e.g., a heat shrink tubing). The non-conductive film 146 simply holds the insulator 140, balun short 142 and conductive film in place on the feedline 102. The conductive film 144 and the non-conductive film 146 are placed such that a distal portion of the insulator 140 extends distally past their respective distal ends. While one embodiment of the ablation probe 100 is described here with respect to FIGS. 1 and 2A, other orientations and constructions are possible without departing from the scope of the present disclosure. One such alternative is described in more detail in U.S. Pat. No. 9,044,254 entitled "MICROWAVE ABLATION CATHETER AND METHOD OF UTILIZING THE SAME," the entire contents of which are incorporated herein by reference. One distinction described in the '254 patent is the use of a braided conductor in place of the conductive film 144 and balun short 142. The braided conductor circumscribes the insulator 140 and is electrically shorted to the outer conductor 130 of the coaxial cable. Another is that rather than the inflow and outflow cooling jackets 108, 110, a catheter having separate inflow and outflow lumen is used and these lumina have orifices proximate the radiating sections 104, 106. The inflow and outflow lumina perform substantially the same function as the cooling jackets 108, 110, but may have one of a variety of arrangements radially around the location of the feedline 102, balun 138, and radiating sections 104, 106.

Figure 2B:
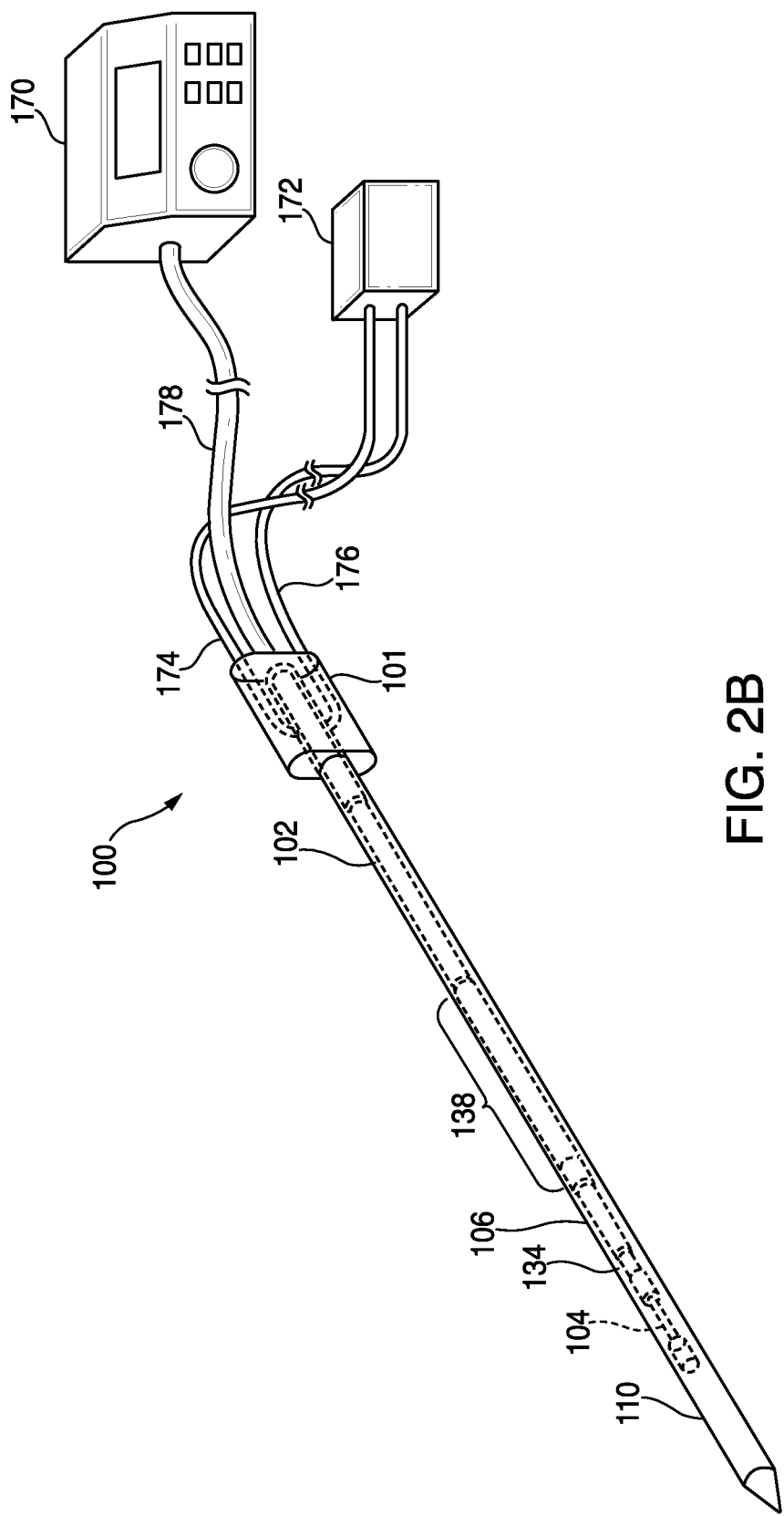
FIG. 2B depicts a microwave ablation system in accordance with at least one aspect of the present disclosure.

The microwave ablation probe 100 is connectable to an energy source 170 and a cooling fluid source 172, as depicted in FIG. 2B. The fluid source 172 connects to catheters 174, 176 to convey fluid to and from the microwave ablation probe 100. Catheters 174 and 176 connect to inflow and outflow ports 112 and 126. Hub 101 of the microwave ablation probe 100 connects the microwave ablation probe 100 to the energy source 170 via a coaxial cable 178. As an example the energy source may be the EMPRINT™ microwave ablation generator.

As noted above, the ablation probe 100 of FIGS. 1 and 2A addresses thermal control and field control, and partially addresses wavelength control. The use of the balun 138 substantially eliminates backwards propagation of electromagnetic waves along the external conductor 130 and thus represents an example of field control. The water jacketing effectively provides for thermal control and helps prevent charring of tissue and sticking of the ablation probe 100 to the tissue into which it is inserted. Finally, the water jacket partially addresses wavelength control. That is, by circulating water through the antenna a portion of field dielectric constant is in fact held substantially constant throughout the treatment process. However, those of skill in the art will immediately recognize that the near field (the area where active ablation can best be controlled by field control) extends well beyond the area of the ablation probe 100, and into the tissue being treated. Thus to effectively provide wavelength control in the entirety of the near field, or at least that portion of the near field which will receive the treatment, the dielectric constant within this field needs to be adjusted to a more constant and predictable value.

The need to adjust the dielectric constant of the near field, or portion thereof, is particularly important in the lung, and in other tissue as well, wherein the dielectric constant across an ablation area can be very different. With respect to the lung, differences in the dielectric constant stem from the fact that in the lung as opposed to other areas of the body there are large volumes of air having a very high dielectric constant. Further, the lungs are very blood rich, and have a larger number of blood vessels. Still further, there is a great deal of mucus produced in the lungs providing yet another material having yet a further dielectric constant. Moreover, each boundary between air, tissue, blood, mucus, etc. creates a boundary effect where further changes in dielectric constant can be observed.

Most microwave ablation probes, because of their construction, and because they treat tissue primarily in the near field, function relatively poorly in areas surrounded by air. In part this is because the power necessary to overcome the dielectric constant results in an undesirable radiation pattern both in the near field and the far field.

One embodiment of the present disclosure is directed at methods and devices that can be used to influence both the dielectric constant in the area where treatment is desired. Two factors to consider when affecting the dielectric constant of tissue are air and hydration. As will be expected, air is primarily only an issue for treatment of the lungs.

To achieve this more consistent dielectric constant, one methodology that is particularly useful for the lungs is to remove the air in the portion of the lung in which treatment is desired. This can be performed by inserting a catheter into the patient's lungs to a desired location proximate the area to be treated. A tamponade can be utilized to separate the area of treatment from the remainder of the lung. This may be an inflatable cuff or other expandable member which can be utilized to form a substantially air tight seal in the airway. A vacuum is then applied to the catheter. Because the tissue of the lungs is generally very flexible, the tissue collapses in the direction of the catheter. The result is the removal of the air, thus eliminating one of the primary dielectric constant influencers in the area to be treated. At this point in the procedure a microwave ablation probe may be either percutaneously or endobronchially inserted into the now collapsed area for treatment and energy can be applied. The details of such systems are presented below.

An alternative to removal of the air from the lungs via a vacuum is to mechanically deform the tissues around the area of interest to compress the target area. In one embodiment, for example, one or more balloons are inserted into airways or into the thoracic cavity such that when inflated they force the tissue in the area to be treated to compress. Such a method relies in part on the physiology of the patient (e.g., rib cage, healthy lung tissue, and the diaphragm) to counter the forces applied by the balloon(s) to force the tissue to be treated to compress in a desired direction, expelling air contained therein and thus achieving a more homogeneous dielectric constant in this area. Instead of balloons, fluids might also be injected to achieve the desired compression. Still further, purely mechanical means, such as one or more mechanical graspers might be deployed from a catheter to grasp and compress the tissue of interest.

A further method of controlling the dielectric constant of tissues in and around an area for treatment is to control the hydration level of the treatment area. This can be done by a variety of means. The first is that an area to be treated can simply be flooded with a fluid such as saline, the result of this flooding is that, in the lung for example, the air is displaced and the dielectric constant of saline, blood, and tissue are much closer to one another, thus the average or mean dielectric constant can be calculated that is more closely representative of the component parts of that average or mean. This value can be used as a basis for power determination for treatment and even for antenna design. Methods of flooding the treatment area are described in greater detail below.

Alternatively, a variety of hydrophobic or hydrophilic materials may be applied to the area of interest to either draw water (bodily fluid) to the area of interest or expel water from the area of interest. For example, application of salts to the area to be treated will have the effect of drawing water out of the salted areas to achieve a homogenous dielectric constant in the salted areas. These methods may be performed a day or more before the treatment to enable the salts or other materials to have time to act on the tissue. As can be appreciated such techniques are possible not just in the lung tissue but in other parts of the body as well.

Figure 3A:
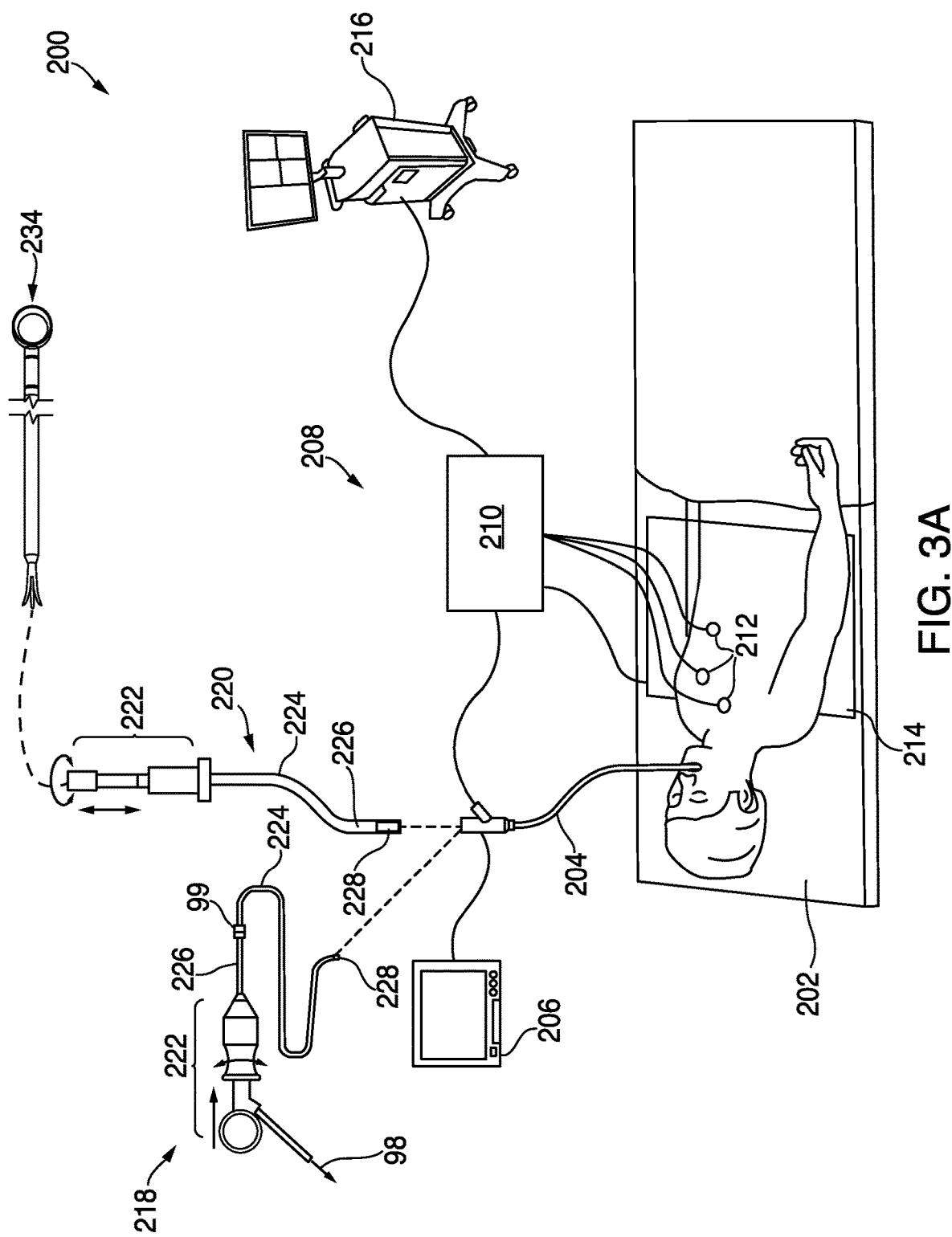
FIG. 3A depicts a schematic view of an electromagnetic navigation system in accordance with at least one aspect of the present disclosure.

FIG. 3A depicts an electromagnetic navigation (EMN) system 200 provided in accordance with the present disclosure. One such EMN system is the ELECTROMAGNETIC NAVIGATION BRONCHOSCOPY® system. Among other tasks that may be performed using the EMN system 200 are planning a pathway to target tissue, navigating a positioning assembly to the target tissue, navigating a tool to the target tissue to obtain a tissue sample from the target tissue using the biopsy tool, digitally marking the location where the tissue sample was obtained, placing one or more echogenic markers at or around the target, and treating the target tissue (e.g., using a flexible microwave ablation probe).

EMN system 200 generally includes an operating table 202 configured to support a patient; a bronchoscope 204 configured for insertion through the patient's mouth and/or nose into the patient's airways; monitoring equipment 206 coupled to bronchoscope 204 for displaying video images received from bronchoscope 204; a tracking system 208 including a tracking module 210, a plurality of reference sensors 212, and an electromagnetic field generator 214; a workstation 216 including software and/or hardware used to facilitate pathway planning, identification of target tissue, navigation to target tissue, and digitally marking the biopsy location FIG. 3A also depicts two types of catheter guide assemblies 218, 220. Both catheter guide assemblies 218, 220 are usable with EMN system 200 and share a number of common components. Each catheter guide assembly 218, 220 includes a handle 222, which is connected to an extended working channel (EWC) 224. EWC 224 is sized for placement into the working channel of a bronchoscope 204. In one embodiment operation, a locatable guide (LG) 226, including an electromagnetic (EM) sensor 228, is inserted into EWC 224 and locked into position such that EM sensor 228 extends a desired distance beyond a distal tip 230 of EWC 224. The location of EM sensor 228, and thus the distal end of EWC 224, within an electromagnetic field generated by electromagnetic field generator 214, can be derived by tracking module 210 and workstation 216. Catheter guide assemblies 218, 220 have different operating mechanisms, but each contain a handle 222 that can be manipulated by rotation and compression to steer distal tip 230 of LG 226 and EWC 224. Catheter guide assemblies 218 are currently marketed and sold under the name SUPERDIMENSION® Procedure Kits. Similarly, catheter guide assemblies 220 are currently under the name EDGE™ Procedure Kits. Both kits include a handle 222, EWC 224, and LG 226. For a more detailed description of the catheter guide assemblies 218, 220, reference is made to U.S. Pat. No. 9,044,254 incorporated by reference above.

As illustrated in FIG. 3A, the patient is shown lying on operating table 202 with bronchoscope 204 inserted through the patient's mouth and into the patient's airways. Bronchoscope 204 includes a source of illumination and a video imaging system (not explicitly shown) and is coupled to monitoring equipment 206, e.g., a video display, for displaying the video images received from the video imaging system of bronchoscope 204.

Catheter guide assemblies 218, 220 including LG 226 and EWC 224 are configured for insertion through a working channel of bronchoscope 204 into the patient's airways (although the catheter guide assemblies 218, 220 may alternatively be used without bronchoscope 204). LG 226 and EWC 224 are selectively lockable relative to one another via a locking mechanism 234. A six degrees-of-freedom electromagnetic tracking system 208, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 208 is configured for use with catheter guide assemblies 218, 220 to track the position of EM sensor 228 as it moves in conjunction with EWC 224 through the airways of the patient, as detailed below.

As shown in FIG. 3A, electromagnetic field generator 214 is positioned beneath the patient. Electromagnetic field generator 214 and the plurality of reference sensors 212 are interconnected with tracking module 210, which derives the location of each reference sensor 212. One or more of reference sensors 212 are attached to the chest of the patient. The coordinates of reference sensors 212 are sent to workstation 216, which includes an application which uses data collected by sensors 212 to calculate a patient coordinate frame of reference.

Also shown in FIG. 3A is a tool 234 (depicted as a biopsy tool but could be any tool such as microwave ablation probe, etc.), that is insertable into catheter guide assemblies 218, 220 following navigation to a target and removal of LG 226. As detailed below, tool 234 is further configured for use in conjunction with tracking system 208 to facilitate navigation of the tool 234 to the target tissue, tracking of tool 234 as it is manipulated relative to the target tissue to obtain the tissue sample and/or treat the target tissue, and/or marking the location where the tissue sample was obtained.

Although navigation is detailed above with respect to EM sensor 228 being included in LG 226 it is also envisioned that EM sensor 228 may be embedded or incorporated within tool 234. In such instances, tool 234 may alternatively be utilized for navigation without need of LG 226 or the necessary tool exchanges that use of LG 226 requires. A variety of useable tools are described in U.S. Patent Published Application Nos. 2015/0141869 and 2015/0141809 both entitled DEVICES, SYSTEMS, AND METHODS FOR NAVIGATING A BIOPSY TOOL TO A TARGET LOCATION AND OBTAINING A TISSUE SAMPLE USING THE SAME, and U.S. patent application Ser. No. 14/564,779 having the same title and filed Dec. 9, 2014, the entire contents of each of which is incorporated herein by reference and useable with EMN system 200 as described herein.

During procedure planning, workstation 216 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 216 or in any other suitable fashion. Using workstation 216, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. Published Patent Application No. 2014/0281,961; 2014/027441; and 2014/0282216, all entitled PATHWAY PLANNING SYSTEM AND METHOD, filed on Mar. 15, 2014, by Baker, the entire contents of each of which is incorporated herein by reference.

During navigation, EM sensor 228, in conjunction with tracking system 208, enables tracking of EM sensor 228 and/or tool 234 as it is advanced through the patient's airways.

Figure 2C:
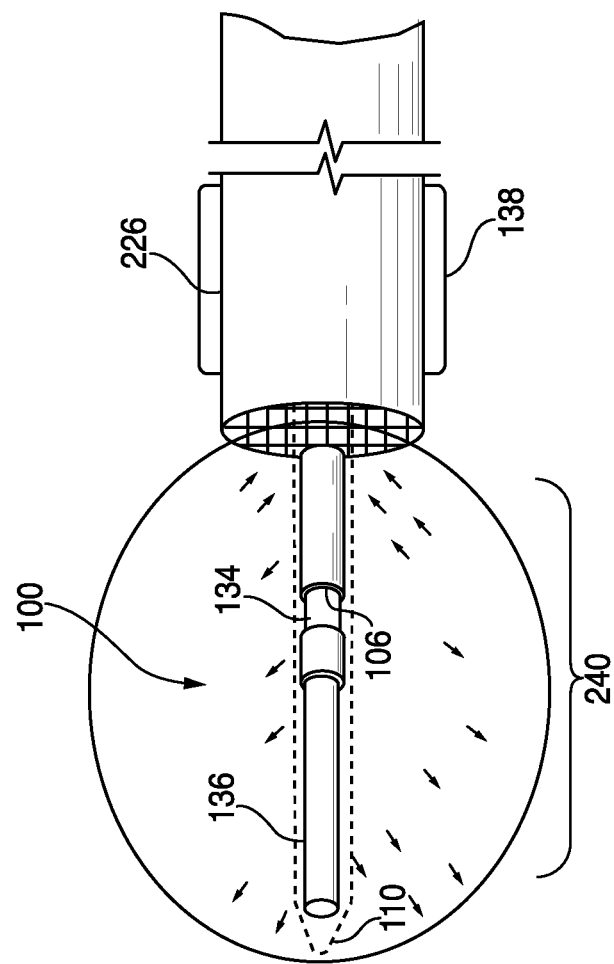
FIG. 2C depicts a detailed view of the distal end of a microwave ablation probe in accordance with at least one aspect of the present disclosure.

As will be appreciated by those of skill in the art, the EWC 224, having been navigated to a location proximate the target tissue can be utilized to supply fluid such as water to flood the target area and thereby affect the dielectric constant in the area. For example, as shown in FIG. 2C, a flexible microwave ablation probe 100 is depicted extending from the distal end of the EWC 224. The flexible microwave ablation probe 100 may have the same or a slightly modified constriction as compared to that depicted in FIGS. 1 and 2A. The microwave ablation probe 100 is depicted as having been inserted into a target area 240. Fluid is depicted as flowing from the EWC 224 to flood the target area 240. As described above, this effect of this fluid is to alter the dielectric constant of the near field around the microwave ablation catheter resulting in more uniform energy distribution and the formation of more uniform spherical ablations. As shown in FIG. 2C the outer cooling jacket 110 is shown with a dashed line representing that it is an optional component of the microwave ablation probe 100. By removing the outer cooling jacket 110 the fluid used to cool the microwave ablation probe 100 is allowed to escape and flood the target area 240. Additionally or alternatively, depending upon size restrictions, fluid can also be supplied directly through the EWC 224. In such an alternative, the inner cooling jacket 108 (not shown in FIG. 2B) might be retained but used as a fluid return in order to maintain cooling flow over the feedline 102 and other portions of the microwave ablation probe 100, to limit the heating of the fluid in the target area 240, and to address changes in the dielectric constant as the fluid heats. Another aspect of this embodiment is that rather than or in addition to the balun being formed on the ablation probe 100, a balun 138 may be placed on the exterior of the EWC 224. This balun 138 could also be shorted to the feedline 102 of the ablation probe 100. The choke 130 on the EWC 224 helps further protect the EWC 224, the bronchoscope 204 (FIG. 3A), and the patient. A similar construction to that described above with respect to FIGS. 1 and 2A may be used for balun 138 formed on the EWC 224.

Yet a further modification contemplated by the present disclosure is the placement of the EM sensor 228 within the outer cooling jacket 110 of the microwave ablation probe 100. As depicted above with respect to FIG. 3A, the LG 226 must be removed from the EWC 224 in order to place a tool 234 such as microwave ablation probe 100 there through. The result is that following removal of the LG the clinician is not completely confident of the location of the EWC 224 or the ablation probe 100. By placing the EM sensor 228 within the microwave ablation probe 100, the precise location of the microwave ablation probe 100 may be determined. However, it has been experienced that the EM sensors 228 are somewhat fragile and can break when being navigated through a tortuous path such as the airways of the lung. Accordingly, rigid placement of the sensor 228 within the ablation probe 100 would result in both the ablation probe 100 and the sensor 228 being rendered inoperable if the sensor 228 were to break. To address this, a removable sensor 228, connected via wire to the proximal end of the microwave ablation probe 100 and removable from within the outer jacket 110 is contemplated. In one embodiment the sensor 228 is located proximate the feed gap 134 but radially away from the radiating sections 104 and 106. This allows for accurate identification and placement of the sensor in the middle of the treatment area 240. On the proximal end of the ablation probe 100, a luer lock or other engagement may be used to allow for removal and insertion of the sensor 228 as necessary. This provides the ability to swap out the sensor 228 if it should break while being navigated with the ablation probe 100 to the target area 240. Though described here as being placed within the ablation probe 100, such a sensor 228 could also be placed in a sidecar arrangement and travel with but outside of the EWC 224 as described in greater detail with respect to FIG. 8.

Figure 4:
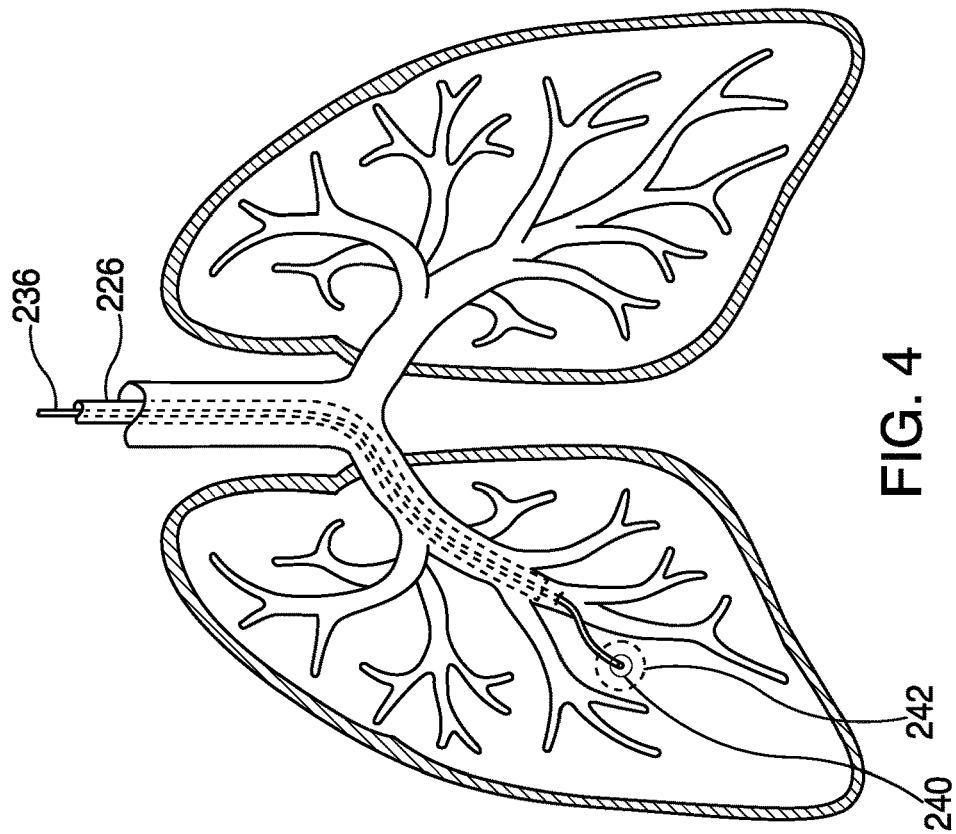
FIG. 4 depicts a cross-sectional view of the lungs undergoing a treatment in accordance with at least one aspect of the present disclosure.

The EWC 224 may also be used to inject salts or other materials (whether hydrophobic or hydrophilic) into the target area 240 to generate an area of reasonably consistent hydration 242, which thus has a definable dielectric constant that can be utilized to perform wavelength control and produce consistent spherical ablations as described above. This may be performed in combination with a needle catheter 236 or other mechanism if piercing of specific tissue is required for the injection as shown in FIG. 4.

Figure 5:
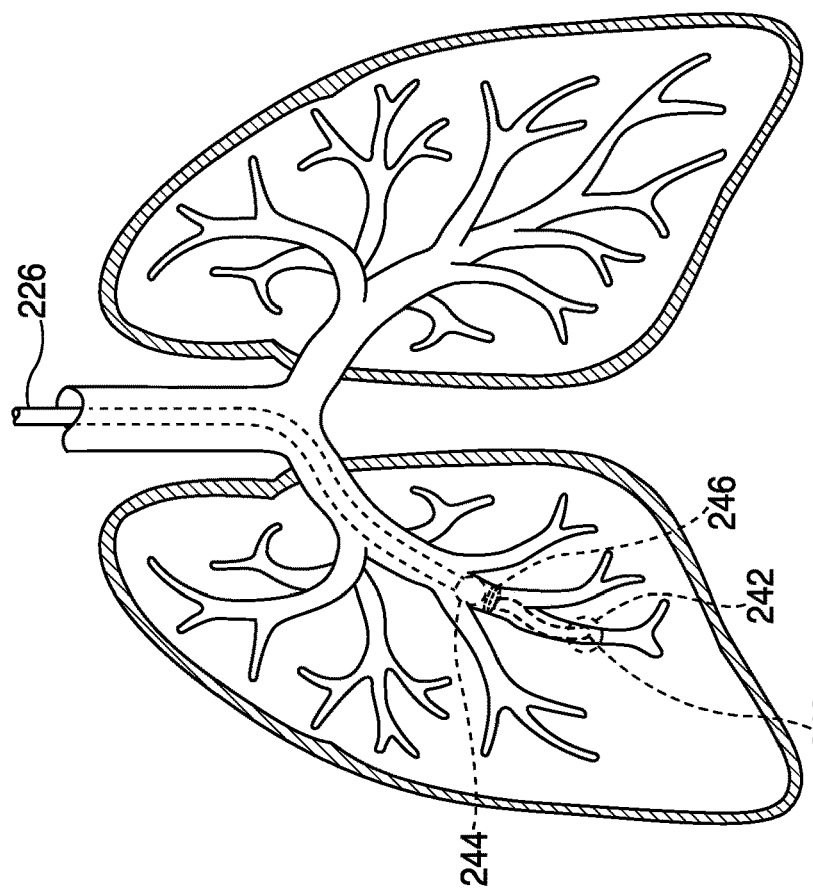
FIG. 5 depicts a cross-sectional view of the lungs undergoing a treatment in accordance with at least one aspect of the present disclosure.

Further, the EWC 224 may be utilized to apply a vacuum and remove air in desired locations within the lung. This may be performed either using a tamponade 244 around the EWC 224, or following placement of one or more one-way valves 246. Tamponade 244 and valve 246 are shown in FIG. 5. As vacuum is applied through the EWC 224, the removal of air collapses the area around the target area 240 and reduces the dielectric constant of the target area 240.

Figure 6:
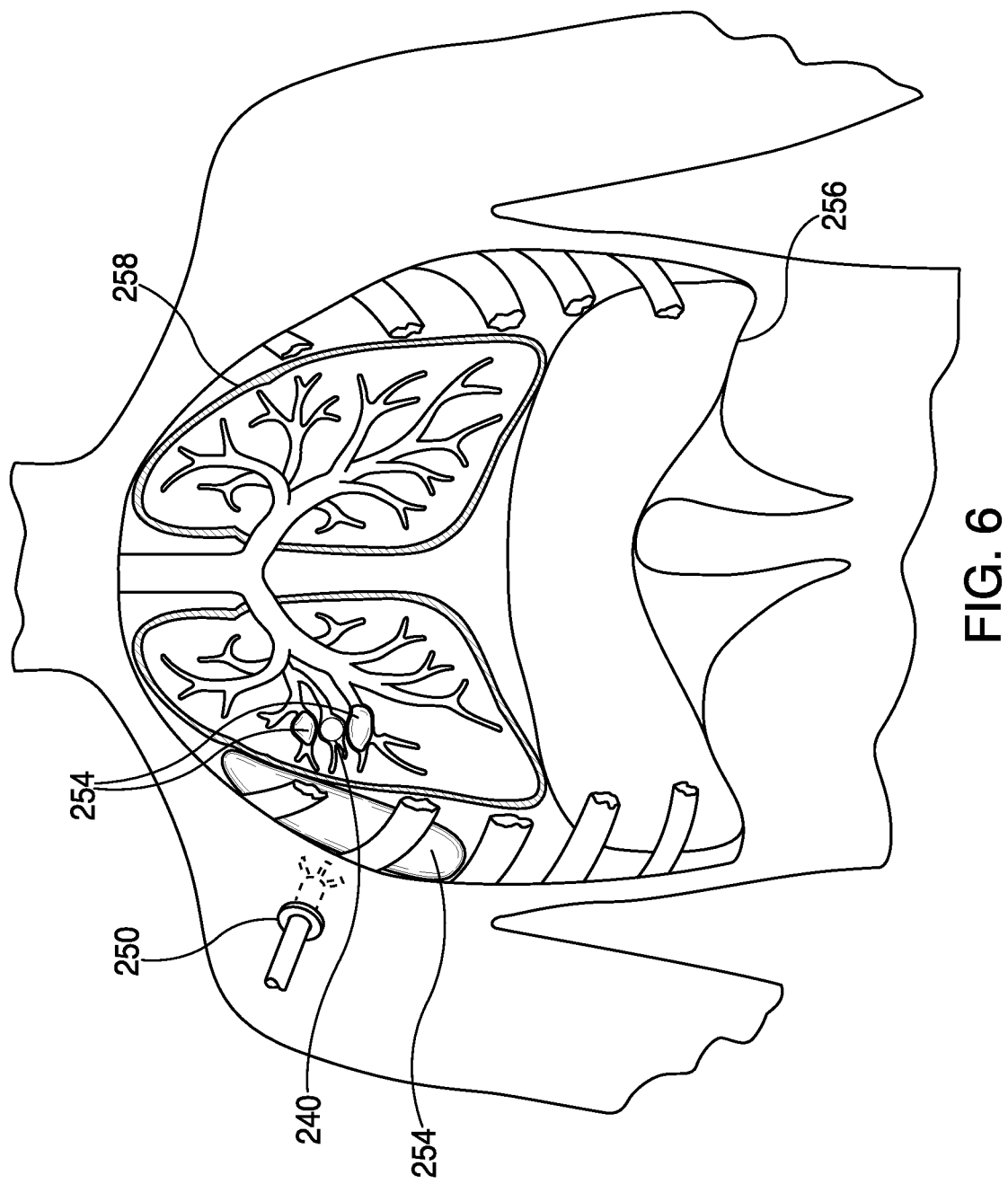
FIG. 6 depicts a cross-sectional view of the lungs undergoing a treatment in accordance with at least one aspect of the present disclosure.

A further embodiment, as noted above is the use of one or more balloons 254 to apply mechanical pressure to the tissue of the lungs. FIG. 6 depicts two such alternatives. According to one, a port 250 is inserted into the patient and a trocar 252 is inserted there through. A balloon 254 is inserted into the chest cavity, outside of the lungs, and inflated. Inflation of the balloon 254 creates pressure against tissue proximate the balloon 254 and limits the amount of room for expansion of the lung tissue. This in combination with the definition of the space in the thoracic cavity by the diaphragm 256 and the lungs 258 works to effectively compress the lung tissue. If appropriately placed, such balloons 254 can be used to compress the tissue in the area of the target 240, force air out of that portion of the lung, and homogenize the dielectric constant of the target area 240. As an alternative the EWC 224 may be used to insert one or more balloons 254 temporarily in portions of the lung within airways or tissue near the target area 240 to produce the same effect as described above. A further alternative to the use of a balloon 254 inserted via the trocar 252 is the use of a compression devices which fits over a lobe or sub-lobal region of the lung and compress the lobe or sub-lobal region to force air out of the region prior to treatment.

As yet a further embodiment, rather than flooding the target area 240 with water or other fluids, tissues proximate the target area 240 may be flooded in order to compress against the target area 240 and force air and mucus out of the target area 240. This may be performed in conjunction with the placement of one or more one-way valves in the airways surrounding the target area 240 to limit flow of the water or other fluid back out of the lungs.

While these techniques are generally described above in the context of treatment of tumors and other lesions in the lungs, particularly for patients suffering from cancer, similar methods may be used for treatment of other diseases such as chronic obstructive pulmonary disorder (COPD). One aspect of COPD is manifest by a breaking down of the structure of the alveoli (air sacks) in the lungs resulting in fewer very larger alveoli (also called emphysema) and by the inflammation of the airways and excess mucus production (also called chronic bronchitis). The result of these conditions, particularly emphysema, is that there is a reduced surface area for the gas exchange to and from the blood. In addition, because the alveoli are breaking down they are no longer resilient and can be overinflated, and over time can begin to simply retain inhaled air because not enough force can be applied to this tissue to force the air back out of alveoli. This results in creating essentially dead spaces in the lungs. However, the lungs are quite resilient and if the damaged portions of the lungs can be treated such that they no longer take up space in the thoracic cavity, the remaining healthier tissue will expand to compensate for the lost lung volume. This approach is currently used in surgical lung volume reduction surgery where entire lung lobes are removed to provide room for the remaining lobes to function As will be appreciated, the systems and methods of the present disclosure may be utilized to treat COPD, particularly emphysema. In one method, one-way valves are placed to enable air to flow out of the alveoli but not back in. Using the balloons, fluid, or other methods of applying pressure to the exterior of the affected alveoli, the air trapped therein can be forced out thus increasing the space in the thoracic cavity for the healthy portions of the lung. Such methods have been suggested before, but the long term insertion of valves and the like in an environment such as the lungs where irritants and infectious material are constantly being inhaled makes such valves a likely source of infection or at minimum inflammation and discomfort for the patient.

The present disclosure provides an alternative approach utilizing the systems and methods described herein. As described above, a EWC can be navigated to a target location 240 and a vacuum can be applied at the target location to collapse the tissue and remove the air. As will be appreciated the fluid or balloon collapsing methods could also be used without departing from the scope of the present disclosure. A microwave ablation probe 100 can then be inserted percutaneously or endobronchially into the collapse target area, but rather than ablating the tissue, the tissue is heated to a sub-lethal temperature. The energy absorbed does need to be sufficient that the tissue does denature and coagulate into a collagen matrix. The result of using this process is that individual alveoli can be identified and targeted and the tissue of the alveoli can be coagulated. Such coagulation effectively removes the alveoli from the pulmonary system and allows for healthy alveoli to compensate similarly as occurs in a lung volume reduction surgery. Indeed, what is described is a very selective lung volume reduction procedure.

In order to achieve the degree of particularity necessary to coagulate individual or small groups of alveoli, one or more control algorithms for predicting and controlling energy source 170 (e.g., the microwave generator) is necessary. U.S. Pat. No. 8,568,401 entitled SYSTEM FOR MONITORING ABLATION SIZE, the contents of which are incorporated herein by reference, teaches a variety of such control algorithms. Specifically, the control algorithm may employ the concept of correlating complex impedance (e.g., real and imaginary portions of the complex impedance) associated with a particular microwave antenna, e.g., microwave ablation probe 100, with target area 240 having a specific radius may be used to indicate tissue death or necrosis. More particularly, complex impedance associated with the microwave ablation probe 100 varies over the course of an ablation cycle due to tissue complex permittivity changes caused by temperature increase. A relationship of complex impedance as a function of time may be defined. When the microwave ablation probe 100 has heated tissue to a maximum attainable temperature, a target area 240 having a corresponding radius is been achieved. At this maximum temperature a dielectric constant and conductivity associated with the ablated tissue reach a steady-state condition (this steady-state condition occurs at time (tss) that corresponds to a steady-state complex impedance (Zss) associated with the microwave ablation probe 100. That is, because the ablated tissue is in a "near field" of the ablation probe 100, the ablated tissue essentially becomes part of the microwave ablation probe 100. Accordingly, when a dielectric constant and conductivity associated with the ablated tissue reaches a steady-state condition, the complex impedance at the microwave ablation probe 100 also reaches a steady-state condition, e.g., Zss, where Zss includes a real portion Zrss and an imaginary portion Ziss.

It should be noted, that Zss may vary for a given microwave antenna. Factors that may contribute to a specific Zss for a given microwave antenna include but are not limited to: dimensions associated with the microwave antenna (e.g., length, width, etc.); type of material used to manufacture the microwave antenna (or portion associated therewith, e.g., a radiating section) such as copper, silver, etc; and the configuration of the radiating section (e.g., dipole, monopole, etc.) and/or a conductive tip (e.g., sharp, blunt, curved, etc) associated with the microwave antenna.

The control algorithm implements one or more model equations to calculate the Zss associated with the ablation probe 100 within a specified time range (e.g., t1-tss) not exceeding tss, i.e., time when the ablated tissue is at the steady-state condition. More particularly, the real and imaginary portions, Zrss and Ziss, respectively, of the Zss of the ablation probe 100 may be calculated via monitoring and/or measuring of a signal (or pulse) generated by the energy source 170. More particularly, a phase (for calculating an imaginary impedance Ziss of the complex impedance) and magnitude (for calculating a real impedance Zrss of the complex impedance) associated with a signal (or pulse) generated by the energy source 170 during an ablation procedure may be sampled and monitored. For example, one or more electrical properties (e.g., voltage, current, power, impedance, etc.) associated with a signal (or pulse) generated by the energy source 170 may be sampled and monitored. For example, in one particular embodiment, forward and reflected power, Pfwd and Pref, respectively, of a signal for ablating tissue is measured by a controller in the energy source 170. Thereafter, the power standing wave ratio (PSWR) is calculated using the equation:

$$PSWR = Pfwd + Pref / Pfwd - Pref \quad (1)$$

where Pfwd is the power associated with the generated signal (i.e., forward signal) and Pref is the power associated with the reflected signal. Those skilled in the relative art can appreciate that with the PSWR, Pfwd and Pref can be used to calculate the complex impedance at the steady-state condition, e.g., Zss, of the microwave ablation probe 100 may be calculated. Specifically, the phase difference between the forward and reflected power may be used to calculate the imaginary portion Ziss of the complex impedance and the magnitude difference between the forward and reflected power may be used to calculate the real portion Zrss of the complex impedance. With Zrss and Ziss known, Zss may be calculated and, subsequently, communicated and/or relayed to a controller in the energy source 170 to determine if a predetermined threshold value Zss that corresponds to a desired ablation size has been met.

In certain instances, known characteristic impedance associated with coaxial cable 178 or other components of the system depicted in FIG. 2B may be employed to determine Zss. More particularly, measurement of Zss may be determined using the equation:

$$Zss - Zo / Zss + Zo = PSWR - 1 / PSWR + 1 \quad (2)$$

where, Zo is the characteristic impedance associated with the coaxial cable 178, for example. The characteristic impedance Zo is an accurate measure of the impedance of the coaxial cable 178 and takes into account the line losses associated with the any connectors, etc. The measurement of Zss will be an accurate representation of the steady-state impedance Zss at the microwave antenna 100 adjacent the ablation zone.

The foregoing algorithms and/or equations are two of many algorithms and/or equations that may be employed to calculate the Zss associated with the microwave ablation probe 100 such that real-time monitoring of an ablation zone may be achieved. For example, one or more model functions ƒ(t) representative of model curves of Zss, Ziss, Zrss, PSWR, Pref or other properties may be utilized in conjunction with the aforementioned equations (or alone) to obtain additional information relevant to Zss. For example a derivative (dz/dt) of a model impedance curve can coaxial cable 178 may provide additional information, e.g., rate of change of complex impedance with respect to time. This rate of change associated with complex impedance with respect to time may be utilized, for example, to determine the time it takes to complete an ablation procedure. Further aspects of controlling the ablation size are described herein below.

Described above are methods of injecting fluid into the treatment area 240. To more readily accomplish this and be able to treat tissue simultaneously, a modified EWC, such as those depicted in FIGS. 7-9 may be warranted. FIG. 7 depicts a bronchoscope 204 having a EWC 224 extending therefrom. Unlike current EWC's being marketed the EWC 224 in FIG. 7 has two lumens. The bottom lumen 260 provides an access point for fluid and/or vacuum to be injected or withdrawn through the EWC 224, whereas the top lumen 262 provides a separate pathway for the LG 226, and tools 234.

FIG. 8 shows an alternative embodiment where a sidecar arrangement is employed. Rather than seek to force an EWC 224 with two lumens of reduced diameter down the working channel of the bronchoscope 204, a second catheter 264 is slidingly attached on the outside of the bronchoscope 204, and fixedly attached on the outside of the EWC 224 during set-up. Once the bronchoscope 204 is wedged in the airways of the patient, the EWC 224 begins its navigation and takes the second catheter 264 which is fixedly attached to the EWC 224 but only slidingly attached to the bronchoscope 204. This allows the second catheter 264 to be drawn along with the EWC 224 (in a sidecar arrangement) as the EWC is navigated to a target area 240, as described above. In one arrangement the second catheter 264 is used to supply fluid, hydrophilic or hydrophobic materials, salts, and/or a vacuum as necessary for a given procedure. The EWC 224 is then free to be used for deployment of the LG 226 and tools 234 such as biopsy and microwave ablation tools.

Still a further embodiment utilizing the two lumens or two catheter system described with respect to FIGS. 7-9 involves the use of one or more grasping tools which may be used to grasp or pierce tissue and draw the tissue towards the EWC for treatment. In FIG. 10A, a grasping/piercing tool 266 extends out of lumen 262 of EWC 224 and includes a plurality of barbed wires 268. These barbed wires 268 expand into the alveoli 502 at the distal end of airway 504 and pierce or affix to the tissue in the alveoli 502. The grasping tool 266 is then withdrawn back into the lumen 262 of the EWC 224 as shown in FIG. 10B. The result is a collapse of the alveoli 502, creating a target area 240 with substantially reduced amounts of air and formed primarily of the tissue of the alveoli 502. A microwave ablation probe 100 (in this case a flexible one) may be inserted into the second lumen 260 and placed within the target area 240 formed of the now collapsed alveoli 502 and energized to treat the alveoli 502. Those of skill in the art will understand that while shown here in the context of a single alveoli 502, the same approach could be undertaken to grasp and collapse a plurality of alveoli or a larger portion of the lung tissue in a single procedure. Further, rather than treating with microwave energy, the collapse alveoli 502 of FIG. 10B could be treated by the application of one or more glues or sealants which can be utilized to prevent the alveoli 502 from returning to its original shape and again affect a reduction in lung volume for the patient.

Described hereinabove are a variety of devices and methods of affecting the dielectric constant of a treatment area 240 in order to generate more predictability in certainty in the formation of spherical ablations. In particular, as described above, the concepts of thermal, field control, and wavelength control have been described in detail. In order to further refine these areas of control a feedback mechanism must be provided. As is known in the microwave ablation arts it is well known to place one or more temperature sensors at locations within a microwave ablation probe 100. For example, FIG. 1 shows one such temperature sensor 148 located in contact with the balun short 142. Such a temperature sensor 148 provides very accurate readings of the temperature of the balun short 142. Similarly temperature sensors 152 are located within the outer cooling jacket 110 that provide an accurate indicator of the temperature of the outer cooling jacket 110 as well as providing an indication of the temperature of the tissue proximate the outer cooling jacket 110. Temperature sensors 152 and 148 may be thermocouples and may be connected back to energy source 170 (FIG. 2B) to provide for control of the energy source.

In addition to sensing temperature, radiometry, which senses emissions from tissue, is also a known technique for interrogating the tissue being treated to determine temperature, state of the tissue, water content and other aspects of the tissue being treated. Typically, either within the energy source 170 (FIG. 2B) or in an in-line component from the feedline 102 to the energy source 170 (FIG. 2B), a radiometer is positioned. Even untreated tissue has certain emissions that can be detected by radiometers. These emissions can serve as a baseline and are simply received via the microwave ablation probe 100 and filtered, detected, and amplified by a radiometer to provide a useful feedback signal identifying properties of the tissue. Additionally or alternatively a non-treatment interrogation signal which is transmitted via the microwave ablation probe 100 to the tissue may be used. This signal is absorbed by the tissue and alters the emissions of the tissue. When the transmission of the interrogation signal is ceased the antenna receives the emissions and again these emissions can be used to create a baseline regarding the properties of the tissue. This baseline can then be compared to the emissions of the tissue following application of microwave energy from the microwave ablation probe 100. Detected changes in emissions can be correlated to changes in the tissue and/or dielectric constant of the target area. This correlation may also involve the detected temperatures described above. The detected change in emissions and temperature feedback provided to the energy source 170 (FIG. 2B) can be used to control the energy source 170 (FIG. 2B), the flow rate of fluid being used to adjust the dielectric constant, identify the need for further application of hydrophobic or hydrophilic materials to the target area, or to determine that the entirety of the target area has been treated and transmission of microwave energy should cease. Further aspects of thermometry and radiometry are described in U.S. Published Patent Application No. 2013/034569 the entire contents of which are incorporated herein by reference.

In a similar fashion reflected power may be determined as a function of the Voltage Standing Wave Ratio (VSWR) which describes the power reflected from the antenna. The smaller the VSWR, the better the antenna is matched to the transmission line and the more power is delivered to the antenna and the tissue surrounding the antenna. As can be appreciated, the dielectric constant surrounding the antenna or in this instance the microwave ablation probe 100 is an important aspect of impedance matching and efficient transmission of energy to the tissue. Accordingly, by detecting changes in the reflected power, determinations can be made with respect to the dielectric constant. This information either alone or in combination with the detected temperature and radiometry information can be used to adjust a wide variety of parameters of the energy source, the flow rate of fluid being used to adjust the dielectric constant, identify the need for further application of hydrophobic or hydrophilic materials to the target area, or to determine that the entirety of the target area has been treated and transmission of microwave energy should cease. The goal of interpretation of these feedback mechanisms is to determine the approximate dielectric constant for a particular target area 240 and to adjust the parameters of the system during the treatment. These feedback measurements may be provided to a vector network analyzer such as those used to analyze components of a microwave antenna system to ascertain specific effects of the tissue, fluid, and other materials in-situ at the target area 240.

An alternative approach to the above is to utilize the data collected above regarding temperature, radiometry and reflected power to design the microwave ablation probe 100 and or plan the ablation procedure with a given microwave ablation probe 100. That is, with a known desired ablation size, for example 2-3 cm diameter, an approximate location of the target area 240 (e.g., lung (central or peripheral), liver, kidney, etc.) and the dielectric constant of the tissue in that area, a map may be created depicting the dielectric constant of the area. This map may then be influenced either by the extraction of air, injection of fluid, collapse of the tissue, and application of hydrophilic or hydrophobic materials such than an ever closer approximation of the dielectric constant of the target area 240 is determined or at least approximated. With this information, a microwave ablation probe 100 can be designed (i.e., impedance matched) and power levels determined specifically for treating the lungs or the liver or other body part to achieve an effective repeatable, and consistent spherical ablation.

As a further aspect of determining the dielectric constant of a given target area 240, using technologies such as real-time CT imaging during an ablation procedure analyses can be undertaken to assess the hydration of the target area 240. With this information the hydration level can be controlled, as discussed above, to maintain the hydration level and therewith the dielectric constant of the target area 240.

Described above in the context of FIG. 3A planning of ablation procedures is an integral portion of effective treatment, particularly within the lungs. In accordance with the present disclosure it is contemplated that the dielectric constants and the desired adaptations of the hydration levels can be made part of a procedure planning application. For large areas of treatment, by being able to consistently and repeatably generate spherical ablations, the planning tool can identify the locations of overlapping spheres, power settings, and hydration requirements to ensure complete and effective ablation of a target area 240. Further, such planning tool can account for the thermal effect of major blood vessels in a target area. Still further by identification of tissue, airways, blood vessels, etc., in the target area an ever more precise determination can be made of the effect of power and time required to effectively treat the tissue. Still further, the plan can provide information on affecting the dielectric constant of the target area 240 to achieve each of the desired ablations. As will be appreciated, such planning may require adaptation as features which had not yet been considered are uncovered during the procedure. For example, based on the reflected power or radiometry it may be determined that a blood vessel has more or less effect than anticipated and the treatment plan may be adjusted accordingly. The goal of such planning systems is to effectively treat all the tissue in the target area with an acceptable safety margin without over treating any portion or extending the treatment beyond the boundaries of the target area 240.

A further aspect of the planning application is that some targets are not effectively treated by a single ablation probe 100 and may best be treated by two probes inserted in parallel into the tissue. This may more frequently occur in the liver and areas where a larger ablation zone is required. In such cases it may be desirable to include in the microwave generator a power splitter to power the two antennas from a single source. The two antennas can also be coupled to a switch which enables one of the antennae to be 90° out of phase with the other. The result is a very different shaped ablation zone. When in phase the ablation will be generally spherical and centered on the end of the ablation probes. Out of phase the ablation zone will be elongated along the ablation probe. Such a configuration enables a very different target area 240 to be effectively treated. Such an effect works particularly well when the microwave ablation probes are quite near one another, for example spaced 10 mm apart or less.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure. While the preceding embodiments were described in terms of bronchoscopy of a patient's airways, those skilled in the art will realize that the same or similar devices, systems, and methods may be used in other lumen networks, such as, for example, the vascular, lymphatic, and/or gastrointestinal networks as well.

The invention claimed is:

1. A system comprising:
   a catheter navigable to a desired location within a patient, the catheter defining a lumen and ending at a distal end of the catheter in an orifice;
   a fluid controller in fluid communication with the lumen of the catheter and configured to control a supply or removal of a fluid to or from an area proximate the desired location via the orifice of the catheter, wherein control of the fluid in the area proximate the desired location affects a dielectric constant of the area proximate the desired location;
   a microwave energy source; and
   a microwave ablation probe operably connected to the microwave energy source, the microwave ablation probe being navigable to the desired location within the patient and movable through the lumen relative to the catheter for placement at the desired location within the patient, the microwave ablation probe including a return lumen configured to return the fluid supplied via the catheter from the area proximate the desired location, wherein application of energy from the microwave energy source to the microwave ablation probe in an area proximate the desired location having the affected dielectric constant results in a substantially spherical tissue effect in the area proximate the desired location.

2. The system of claim 1, further comprising an electromagnetic navigation system to facilitate navigation of the catheter and the microwave ablation probe to the desired location.

3. The system of claim 2, wherein the catheter or the microwave ablation probe includes an electromagnetic sensor associated with the electromagnetic navigation system to identify its location in an electromagnetic field.

4. The system of claim 1, wherein the fluid controller includes a vacuum source.

5. The system of claim 4, wherein the vacuum source is configured to apply suction via the catheter to the area proximate the desired location to affect the dielectric constant of the area proximate the desired location.

6. The system of claim 5, wherein the suction removes one or more of air, blood, or mucus.

7. The system of claim 1, wherein the fluid controller is a fluid supply.

8. The system of claim 7, wherein the fluid supply is configured to inject a fluid into the area proximate the desired location to affect the dielectric constant of the area proximate the desired location.

9. The system of claim 8, wherein the fluid is saline.

10. The system of claim 8, wherein the fluid includes a hydrophilic component to attract bodily fluid to the area proximate the desired location.

11. The system of claim 10, wherein the hydrophilic component is a salt.

12. The system of claim 7, wherein the fluid includes a hydrophobic component to repel bodily fluids away from the area proximate the desired location.

13. The system of claim 1, further comprising a one-way valve configured to be inserted in the patient proximate the desired location, wherein the one-way valve prevents fluid from flowing from the area proximate the desired location into which the fluid was supplied.

14. The system of claim 1, further comprising a tamponade configured to be inflated proximate the desired location, wherein the tamponade prevents fluid from flowing out of the area proximate the desired location into which the fluid was supplied.

15. The system of claim 1, wherein the dielectric constant of the fluid supplied to the area proximate the desired location is substantially the same as that of a cooling fluid circulating through the microwave ablation probe.

16. The system of claim 15, wherein a distal end of the microwave ablation probe is exposed and the cooling fluid for the microwave ablation probe is used as the fluid injected into the area proximate the desired location to affect the dielectric constant of the area proximate the desired location.

17. The system of claim 1, further comprising a balun formed on the microwave ablation probe to control an electromagnetic field emanating from the microwave ablation probe.

18. The system of claim 1, wherein a flow rate of the fluid into the area proximate the desired location is adjusted based on at least one of a detected emission and a detected temperature.

19. The system of claim 1, further comprising a display configured to display a map depicting the dielectric constant in the area proximate the desired location is created based in part on fluid injected into the area proximate the desired location.

20. The system of claim 1, further comprising a balun disposed on the catheter.

* * * * *

UNITED STATES PATENT AND TRADEMARK OFFICE
CERTIFICATE OF CORRECTION

Page 1 of 1

| | |
|---|---|
| PATENT NO. | : 10,792,100 B2 |
| APPLICATION NO. | : 14/831467 |
| DATED | : October 6, 2020 |
| INVENTOR(S) | : Joseph D. Brannan |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1149 days.

Signed and Sealed this
Eighteenth Day of February, 2025

Coke Morgan Stewart
*Acting Director of the United States Patent and Trademark Office*